(12) United States Patent
Luo

(10) Patent No.: US 11,975,150 B1
(45) Date of Patent: May 7, 2024

(54) DEVICE FOR DELIVERING GAS

(71) Applicant: DCSTAR INC, New York, NY (US)

(72) Inventor: David Luo, New York, NY (US)

(73) Assignee: DCSTAR INC, New York, NY (US)

( * ) Notice: Subject to any disclaimer, the term of this patent is extended or adjusted under 35 U.S.C. 154(b) by 0 days.

(21) Appl. No.: 18/324,263

(22) Filed: May 26, 2023

(51) Int. Cl.
*A61M 16/06* (2006.01)
*A61M 16/08* (2006.01)

(52) U.S. Cl.
CPC .... *A61M 16/0605* (2014.02); *A61M 16/0816* (2013.01); *A61M 2205/42* (2013.01)

(58) Field of Classification Search
CPC ... A41D 13/1146; A61B 5/0836; A61B 5/097; A61M 16/0003; A61M 16/06; A61M 16/0616; A61M 16/0633; A61M 16/065; A61M 16/0683; A61M 16/0816; A61M 16/0825; A61M 16/0833; A61M 16/085; A61M 16/0866; A61M 16/1045; A61M 16/105; A61M 16/1065; A61M 16/208; A61M 2202/0007; A61M 2202/0085; A61M 2202/0208; A61M 2202/0225; A61M 2205/0227; A61M 2205/18; A61M 2205/42; A61M 2205/6045; A61M 2205/75; A61M 2209/06; A61M 2230/43; A61M 2230/432; A62B 18/006
See application file for complete search history.

(56) References Cited

U.S. PATENT DOCUMENTS

| | | | | |
|---|---|---|---|---|
| 3,130,722 A | * | 4/1964 | Dempsey | A41D 13/1146 128/206.28 |
| 6,581,594 B1 | * | 6/2003 | Drew | A61M 16/0644 128/207.12 |
| 2003/0047188 A1 | * | 3/2003 | Mace | A61M 16/0841 128/204.23 |
| 2008/0142001 A1 | * | 6/2008 | Wright | A61M 16/08 128/207.14 |
| 2009/0250060 A1 | * | 10/2009 | Hacke | A61M 16/06 128/205.12 |
| 2010/0154798 A1 | * | 6/2010 | Henry | A61M 16/065 128/206.24 |
| 2016/0296720 A1 | * | 10/2016 | Henry | A61M 16/0066 |
| 2019/0038863 A1 | * | 2/2019 | Chang | A61M 16/1065 |

* cited by examiner

*Primary Examiner* — Annette Dixon
(74) *Attorney, Agent, or Firm* — HSML P.C.

(57) ABSTRACT

A device for delivering gas includes a frame, a gas delivery hose, and a noise reduction component. The gas delivery hose is detachably connectable to the frame. The noise reduction component includes a ventilation port and a muffler. The ventilation port is provided in communication with the cavity of the frame, and the muffler is connected to the frame and covers the ventilation port. The muffler has a first surface having a first breathable area exposed to the external environment, and a second surface having a second breathable area exposed to the cavity. The muffler also has multiple breathable channels connecting the first breathable area and the second breathable area, allowing gas in the cavity to be discharged from the muffler to the external environment. The multiple breathable channels in the muffler can disperse the gas flow, making it less turbulent and reducing the noise generated.

20 Claims, 11 Drawing Sheets

DEVICE FOR DELIVERING GAS

TECHNICAL FIELD

The present disclosure relates to the field of medical devices, specifically to medical equipment related to obstructive sleep apnea, and more specifically, to a device for delivering gas.

BACKGROUND

Obstructive sleep apnea is a common sleep-related breathing disorder characterized by breathing pauses and low airflow due to narrow airways. This disease can cause breathing pauses in patients during sleep. In adults, there are at least 30 breathing pauses per night for 7 hours of sleep time, with each episode lasting for at least 10 seconds of cessation of nasal and oral airflow. During breathing pauses, oxygen saturation drops by more than 4% or the apnea-hypopnea index is greater than 5 times per hour. Obstructive sleep apnea can cause chronic intermittent hypoxia and fragmented sleep, resulting in a series of physiological changes such as hypoxemia, hypercapnia, and is prone to cause multi-system damage or complications such as coronary heart disease, hypertension, and diabetes.

Continuous positive airway pressure ventilation is a way to treat obstructive sleep apnea. Pressurized air is generated by a ventilator, transported through a ventilator hose, and delivered to the patient's breathing cavity to open the airway and restore normal breathing. In the treatment process, another component, a frame component, is also used. The frame component is generally used to deliver the pressurized gas to the patient's nasal mask. The ventilator hose transports pressurized gas to the frame hose, which then transports the pressurized gas to the frame and nasal mask, transmitting it to the patient's breathing cavity to achieve the therapeutic effect.

In some cases, this treatment system may include a ventilation port device to allow carbon dioxide to be exhaled. The ventilation port device can allow gas to flow from the inside of the patient interface to the outside of the patient interface, for example, to the environment. Once this processing system starts running, a relatively sealed environment is formed, and the patient's inhalation and exhalation are completed in this small space. If the device does not have a ventilation port or the design of the ventilation port is not reasonable, it is easy to inhale carbon dioxide again or even cause or worsen the retention of carbon dioxide in this environment, which is very detrimental to health. In the event of sudden power outages and other emergencies, the ventilation port device can be used for ventilation and breathing to prevent suffocation.

Therefore, the ventilation port device is a very important structure in the entire continuous positive airway pressure ventilation therapy device. For patients or partners sharing beds with the patients, the noise generated by exhaust is an important issue during the treatment process. Excessive noise can make it difficult for patients to fall asleep. The ventilation port device commonly used in the market now is to directly perforate the mask, elbow, or frame, and the exhaled gas is directly discharged from the hole, resulting in relatively concentrated airflow and easy noise production (There are holes on the mask, elbow, or frame that penetrate from the inner surface to the outer surface, and there are no attachments on the inner and outer surfaces of the opening area). Moreover, if the perforation design is not appropriate, a whistling sound may be emitted when the gas flows through the hole, and excessive noise can make it difficult for patients to fall asleep and easily affect sleep quality.

SUMMARY

The present disclosure relates to a device for delivering gas. The device is designed to disperse gas flow, reduce noise during gas discharge, improve sleep quality, and enhance user experience. Additionally, the device is easy to clean, reduces resource waste, and is user-friendly during the treatment process.

To address the aforementioned technical issues, the device for delivering gas includes a frame with a first side connecting the nasal mask and a second side opposite to the first side. The frame and a nasal mask form a cavity. A gas delivery hose has an exhaust end connector detachably connectable to the second side of the frame and an intake end connector for connection with a breathing machine hose. Both ends of the exhaust end connector are connected to the intake end connector and the cavity. The noise reduction component includes a ventilation port and a muffler. The ventilation port is opened in the frame and connected to the cavity. The muffler is connected to the frame and covers the ventilation port. The muffler has a first surface facing the external environment and a second surface opposite to the first surface. The first surface has a first breathable area exposed to the external environment, and the second surface has a second breathable area exposed to the cavity. The muffler also has multiple breathable channels that connect the first breathable area and the second breathable area, allowing gas in the cavity to be discharged to the external environment through the muffler.

By using the device described above, a breathing machine hose transports pressurized gas to the gas delivery hose, which then transports the pressurized gas to the frame and nasal mask for delivery to the patient's respiratory tract, achieving the desired treatment effect. One of the advantages of the present disclosure is that at least one noise reduction component is used to replace the current technology of opening holes directly on the frame or elbow. One of the key advantages is that the noise reduction component includes a muffler and a ventilation port that penetrates the frame to connect the cavity with the external environment. The muffler is connected to the frame and covers the ventilation port and can be made of noise reduction materials. Specifically, the muffler has a first surface and a second surface, where the first surface corresponds to the side facing the external environment, and the second surface corresponds to the side facing the cavity (referred to as the pressurization chamber in this field) and the face. Additionally, the muffler has multiple ventilation channels that connect the first breathing area and the second breathing area. It can be understood that the gas generated by human exhalation enters the cavity and forms a separate exhaust flow path from the pressurized airflow in the cavity. The exhaled gas is smoothly (where the exhaled gas is less turbulent) guided to the noise reduction component and enters the external environment through the ventilation channels of the muffler, allowing the gas in the cavity to be discharged to the external environment through the muffler. Therefore, when the device is worn, the exhaled gas, such as carbon dioxide, can continuously flow out of the inside of the cavity (referred to as the pressurization chamber in this field) through the noise reduction component and into the external environment. The multiple ventilation channels in the muffler can disperse the airflow and reduce the sound when the gas in the cavity is discharged through the muffler to the external environment, significantly reducing noise. Additionally, by setting the noise reduction component, the probability of carbon dioxide being inhaled again during exhalation can be reduced, and the therapeutic pressure in the cavity can be maintained during use.

It is worth mentioning that there are other products on the market that use textiles in their frame to achieve an exhaust function. However, the hose for these products is permanently connected to the frame and cannot be detached or rotated. In contrast, the proposed technology in this application allows for detachable connections between the exhaust end connector of the hose and the frame, which provides several advantages. Firstly, it is more convenient for daily wearing and removal. When users need to leave the bed temporarily, they can detach the hose without removing the frame that holds the nasal mask in place, thus avoiding the tedious process of readjusting the nasal mask. Moreover, an integral frame and hose can have sanitation blind spots or cleaning agent residues, and it is difficult to dry after cleaning, which increases the likelihood of bacterial growth. A detachable design allows for easy separation of the hose and frame, making it more convenient to clean and dry. Secondly, an integral frame and hose are more susceptible to damage. Considering the service life of both components, the hose is more prone to stretching and puncture due to its material, making it easier to damage. If the hose is damaged, the frame needs to be replaced as well, which reduces the service life of the entire device. The detachable design increases modularity, allowing for replacement of individual components without replacing the entire device. This improves the product's service life, saves resources, and reduces users' costs.

The above-described device for delivering gas provides a first breathable area with a surface area of at or between 3% to 72% of the outer surface area of the frame on the second side, where the contour of the ventilation port can be circular, elliptical, rectangular, square, or triangular. This ensures that there is enough space for the gas inside the cavity to be discharged smoothly to the external environment without compromising the overall structural strength of the frame. The airflow direction from the noise reduction component should avoid blowing toward the user's face or other areas that could affect the user's sleep, and also avoid blocking the ventilation port when sleeping on the side.

The frame of the device for delivering gas has a shielding wall with a thickness of less than or equal to 7 mm (that is, no more than 7 mm) and the ventilation port is provided in the shielding wall. The muffler has a thickness of less than or equal to 10 mm (that is, no more than 10 mm) and a weight of less than or equal to 7.5 g (that is, no more than 7.5 mm). The first breathable area or the second breathable area has a surface area at or between 1-21 $cm^2$. The muffler is made of noise-reducing cotton or noise-reducing mesh, made of one of polyester, polypropylene, polyethylene, nylon, vinylon, or natural fabric for noise-reducing cotton, and one of polyvinyl chloride, polypropylene, polytetrafluoroethylene, or nylon for noise-reducing mesh. The material, thickness, and density of the muffler determine its noise reduction effect, but the specific design needs to be collectively determined based on processing, aesthetics, and actual effect. The thickness of the material of the muffler should not be too thick, as it will reduce the gas permeability and affect the appearance and weight of the overall mask. Therefore, the thickness of the noise-reducing material (i.e., muffler) is at most 10 mm, and the weight is at most 7.5 g. The thickness of the noise-reducing material refers to the perpendicular distance from the first surface to the second surface of the noise-reducing material. With this design, the noise generated when the exhaled gas passes through the muffler and enters the external environment does not exceed 30 dB.

In the device for delivering gas provided in this application, the exhaust end connector is rotatably connected to the second side of the frame, while the intake end connector is detachably and rotatably connectable to the breathing machine hose. This allows for convenient use in multiple ways. Furthermore, the gas delivery hose is rotatably connected to the breathing machine hose via the intake end connector, and the design of the rotatable ends of the gas delivery hose facilitates adjustment of the angle and position of the hose to avoid tangling and to allow for various wearing styles, providing a better user experience.

In the device for delivering gas provided in this application, the intake end connector and the exhaust end connector are connected by a telescopic tube, the cross-sectional contour of which is circular, and the outer diameter range of the telescopic tube is at or between 10-40 mm, with a diameter range of at or between 0.5-10 mm. It should be noted that there is a helical coil on the telescopic tube, and the diameter range refers to the diameter of the helical coil.

In the device for delivering gas provided in this application, the frame is equipped with a buckle connector, and the detachable nasal mask is fastened to the buckle connector. Here, the frame is at least partially rigid, and the buckle connector is located in the rigid part of the frame, allowing for the detachable connection of the frame and the nasal mask.

The above-mentioned device for delivering gas provided in this application includes a noise reduction component, which also comprises a shell. The muffler is attached to one side surface of the shell facing the cavity, and the shell has at least one through exhaust port. The shell can be detachably connected to the frame by adhesive, buckle, Velcro, knob, magnetic suction device, or clip. Therefore, when the air permeability of the muffler is found to be reduced, it can be quickly replaced or cleaned without processing the entire frame.

In the above-mentioned device for delivering gas provided in this application, the muffler is fixedly connected to the frame. The inner surface of the frame is located on the first side. Specifically, the connection between the muffler and the frame is achieved by adhesive (using glue or other adhesive to attach the muffler 41 to the frame 3), buckle, knob, clip (constructing clips on the muffler 41 and the frame 3 to connect them together), ultrasonic pressure bonding (using an ultrasonic machine to connect the muffler 41 with the frame 3) or compression, or heat or hot pressing. Therefore, the connection between the muffler and the frame is more stable and less likely to fall off.

To solve the above technical problems, the disclosure provides another device for delivering gas, including: a frame with a first side connecting the nasal mask and a second side opposite to the first side, the frame and the nasal mask forming a cavity; a gas delivery hose with an exhaust end connector detachably connectable to the second side of the frame and an intake end connector for docking with a ventilator hose, and the two ends of the exhaust end connector are respectively connected to the intake end connector and the cavity; a noise reduction component comprising a ventilation port and a muffler, the ventilation port being provided on the exhaust end connector and communicating with the cavity, the muffler being connected to the exhaust end connector and covering the ventilation port, the muffler having a first surface facing the external environment and a second surface opposite to the first surface, the first surface having a first breathable area exposed to the external environment, and the second surface having a second breathable area exposed to the internal space of the exhaust end connector. The muffler also has multiple breathable channels connecting the first breathable area and the second breathable area, allowing gas in the cavity to be discharged to the external environment through the muffler.

Obviously, when wearing the device, the gas exhaled by the human body, such as carbon dioxide, can continuously be discharged from the interior of the cavity (referred to as a pressurization chamber in this field) to the external environment through the noise reduction component. The multiple breathable channels contained in the muffler can disperse the gas flow, making the concentrated gas flow dispersed into smaller and less turbulent gas flows, thereby significantly reducing the noise when the gas inside the cavity is discharged to the external environment through the muffler, and achieving a significant noise reduction effect.

To tackle the above technical problem, the disclosure provides another device for delivering gas, including a frame with a first side connecting the nasal mask and a second side opposite to the first side, where the frame and the nasal mask form a cavity; a gas delivery hose with an exhaust end connector detachably connectable to the second side of the frame and an intake end connector for docking with the breathing machine hose, where the two ends of the exhaust end connector are respectively connected to the intake end connector and the cavity; a noise reduction component including a ventilation port and a muffler, where the ventilation port is opened in the frame and connected to the cavity, and the muffler is connected to the frame and covers the ventilation port, and the muffler has a first surface facing the external environment and a second surface opposite to the first surface, where the first surface has a first breathable area exposed to the external environment, and the second surface has a second breathable area exposed to the cavity; the muffler also has multiple breathable channels that connect the first breathable area and the second breathable area, allowing the gas in the cavity to be discharged to the external environment through the muffler component; where the surface area of the first breathable area is at or between 3% to 72% of the outer surface area of the frame, and the outer surface of the frame is located on the second side; the frame has a shielding wall with a thickness less than or equal to 7 mm, and the ventilation port is opened in the shielding wall.

In another embodiment, to deal with the above technical problems, a device for delivering gas is provided, including: a frame having a first side connecting the nasal mask and a second side opposite the first side, wherein the frame and the nasal mask form a cavity; a gas delivery hose with an exhaust end connector detachably connectable to the second side of the frame and an intake end connector for connecting with a breathing machine hose, wherein both ends of the exhaust end connector are connected to the intake end connector and the cavity, respectively; a noise reduction component comprising a ventilation port and a muffler, wherein the ventilation port is provided on the frame and communicates with the cavity, and the muffler is connected to the frame and covers the ventilation port, and has a first surface facing the external environment and a second surface opposite the first surface, in which the first surface has a first breathable area exposed to the external environment, and the second surface has a second breathable area exposed to the cavity; the muffler further includes multiple breathable channels communicating with the first breathable area and the second breathable area, thereby allowing gas in the cavity to be discharged to the external environment through the muffler. The muffler is a thin sheet having a thickness less than or equal to 10 mm; the area of the first breathable area or the second breathable area is at or between 1-21 $cm^2$; and the weight of the muffler is less than or equal to 7.5 g.

In yet another embodiment, to solve the above technical problems, a device for delivering gas is also provided, including: a frame having a first side connecting the nasal mask and a second side opposite the first side, wherein the frame and the nasal mask form a cavity; a gas delivery hose having an exhaust end connector detachably connectable to the second side of the frame and an intake end connector for connecting with a breathing machine hose, where both ends of the exhaust end connector are connected to the intake end connector and the cavity, respectively; a noise reduction component including a ventilation port and a muffler, where the ventilation port is provided on the frame and communicates with the cavity, and the muffler is connected to the frame and covers the ventilation port, and has a first surface facing the external environment and a second surface opposite the first surface, where the first surface has a first breathable area exposed to the external environment, and the second surface has a second breathable area exposed to the cavity; the muffler further includes multiple breathable channels communicating with the first breathable area and the second breathable area, thereby allowing gas in the cavity to be discharged to the external environment through the muffler. The exhaust end connector is rotatably connected to the second side of the frame.

As such, the implementation of the device for delivering gas according to the present disclosure can achieve at least the following beneficial effects:

1) The device is equipped with at least one noise reduction component to replace the conventional method of directly opening holes on the frame. One of the keys is that the noise reduction component includes a ventilation port and a muffler. The ventilation port penetrates the frame to connect the cavity with the external environment. The muffler is connected to the frame and covers the ventilation port, which can be made of noise reduction materials. Specifically, the muffler has a first surface facing the external environment and a second surface facing the cavity (referred to as the pressurization chamber in the field) and the face. Moreover, the muffler has multiple breathable channels that communicate with the first and second breathable areas. It can be understood that the gas exhaled by the human body enters the cavity and forms a different exhaust flow path from the pressurized airflow. The exhaled gas is smoothly guided to the noise reduction component and enters the external environment through the breathable channels of the muffler. Therefore, when the device is worn, the exhaled gas, such as carbon dioxide, can continuously be discharged from the inside of the cavity (referred to as the pressurization chamber in the field) to the external environment through the noise reduction component. The multiple breathable channels contained in the muffler can disperse the gas flow and turn the concentrated gas flow into a smaller and less turbulent gas flow, which significantly reduces the noise when the gas in the cavity is discharged to the external environment through the muffler, achieving a significant noise reduction effect.

2) Furthermore, because the gas exhaled by the human body can continuously flow from the interior of the cavity to the external environment, setting the noise reduction component can reduce the probability of the exhaled carbon dioxide being inhaled again, while also maintaining the therapeutic pressure in the cavity during use.

3) The device is more convenient for daily wearing and removal. When temporarily leaving the bed, the user can remove the delivery hose without having to take off the frame that fixes nasal mask, thus avoiding the tedious process of readjusting the nasal mask.

4) The integrated frame and delivery hose of prior solutions cannot be separated, which can lead to hygiene blind spots or residual from cleaning agents left during the cleaning process, and can make it difficult to dry after cleaning, making it more prone to bacterial growth. The detachable design allows the delivery hose and the frame to be separated, making cleaning and drying more convenient.

5) The integrated frame and delivery hose are more prone to damage. In terms of the service life of the two, the delivery hose is more susceptible to stretching and piercing due to its material, making it more prone to damage. If the delivery hose is damaged, the frame also needs to be replaced, which will reduce the service life of the entire device. After the addition of the detachable design in this application, the product becomes modular, and if one component is damaged, a replacement can be sought without replacing the entire device, thereby increasing the product's service life and saving resources, reducing user costs.

BRIEF DESCRIPTION OF THE DRAWINGS

To better illustrate the technical solutions in the embodiments or the prior art, the following briefly introduces the drawings that need to be used in the description of the embodiments or the prior art. Obviously, the following described drawings are only embodiments of the disclosure, and ordinary skilled persons in the field can obtain other drawings based on the provided drawings.

Figure 1:
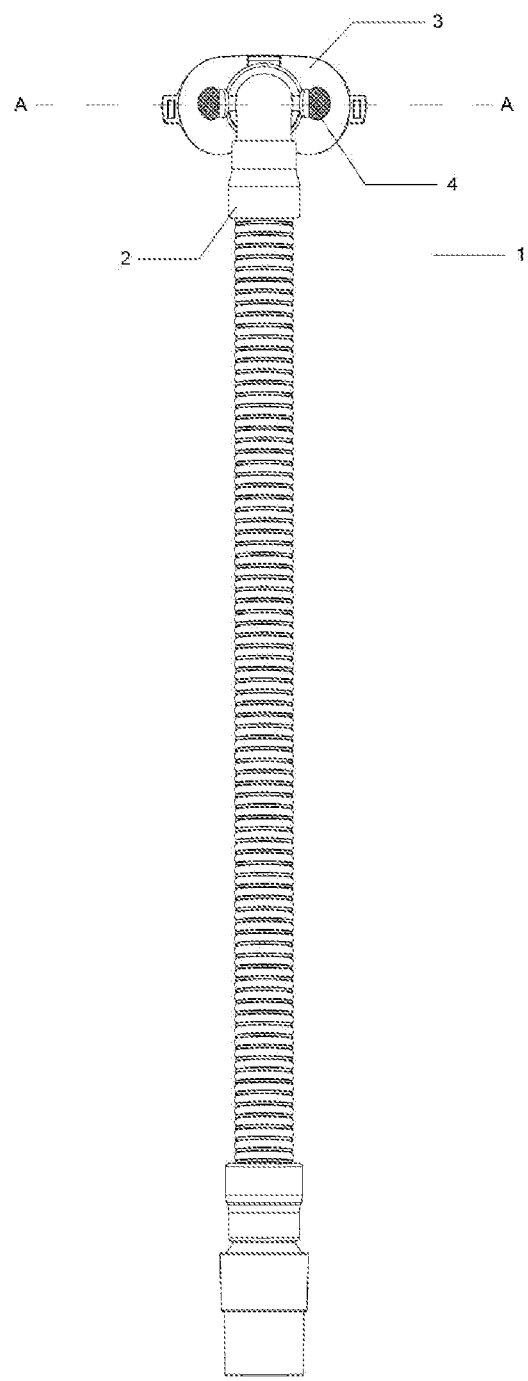
FIG. 1 is a schematic diagram of the front view of a device for delivering gas provided in Embodiment 1.

Description of reference numerals in specific implementations:

| Device | 1 | Gas delivery hose | 2 |
|---|---|---|---|
| Frame | 3 | Noise reduction component | 4 |
| Headband | 5 | Nasal mask | 6 |
| Exhaust end connector | 21 | Intake end connector | 22 |
| Telescopic tube | 23 | The first connector | 211 |
| The second connector | 221 | | |
| Frame body | 31 | Buckle connector | 32 |
| cylindrical protruding interface | 33 | Buckle | 331 |
| Muffler | 41 | Ventilation port | 42 |
| First surface | 411 | Second surface | 412 |
| Circular positioning barrier | 212 | Hooking piece | 213 |
| Hook portion | 2131 | Pressing portion | 2132 |
| Supporting piece | 2133 | | |

DETAILED DESCRIPTION

To facilitate understanding of the disclosure, a more comprehensive description of the disclosure will be given with reference to the accompanying drawings. The drawings show typical embodiments of the disclosure. However, the disclosure can be implemented in many different forms and is not limited to the embodiments described in this article. On the contrary, the purpose of providing these embodiments is to make the disclosure of the disclosure more thorough and comprehensive.

Unless defined otherwise, all technical and scientific terms used in this disclosure have the same meaning as understood by those skilled in the art of the technology field to which the disclosure belongs. The terms used in the specification of the disclosure are used only for the purpose of describing specific embodiments and are not intended to limit the disclosure.

Embodiment 1

Figure 2:
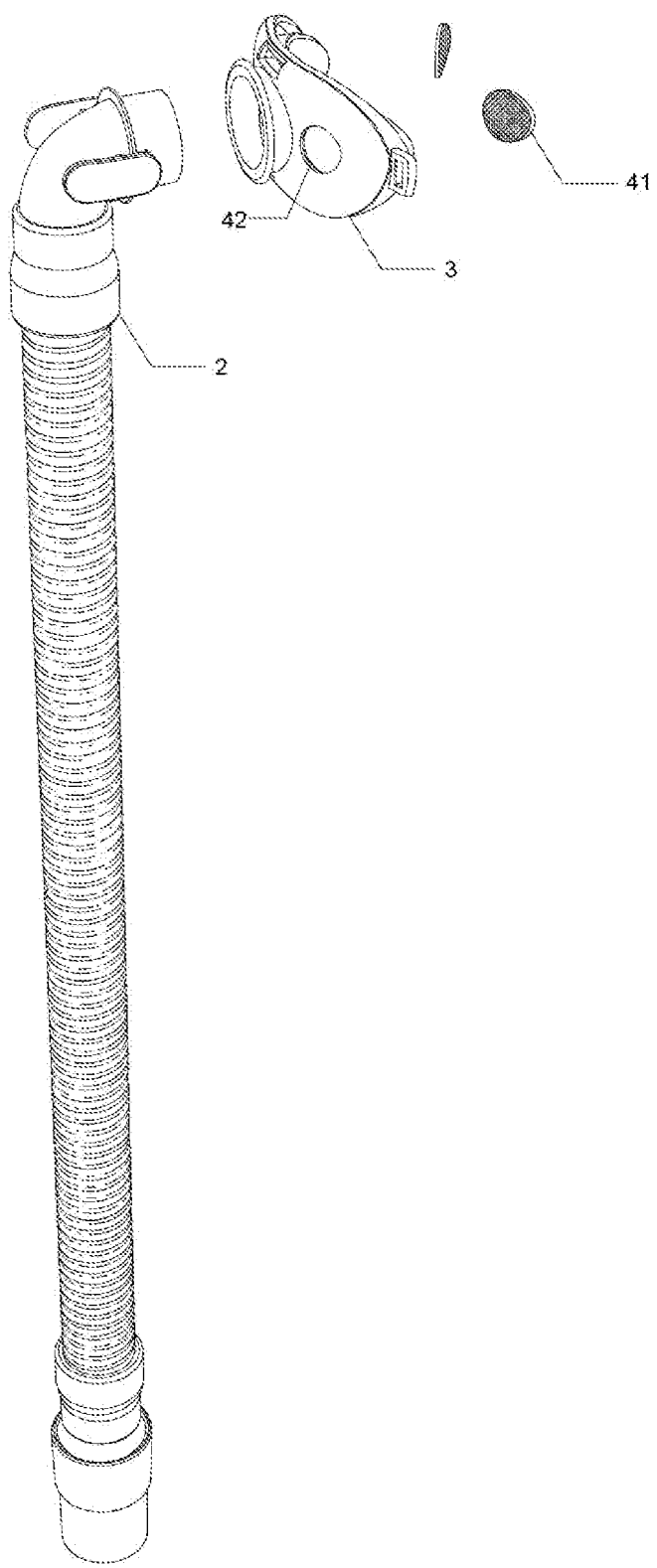
FIG. 2 is a three-dimensional exploded schematic diagram of the device for delivering gas provided in Embodiment 1.
Figure 3:
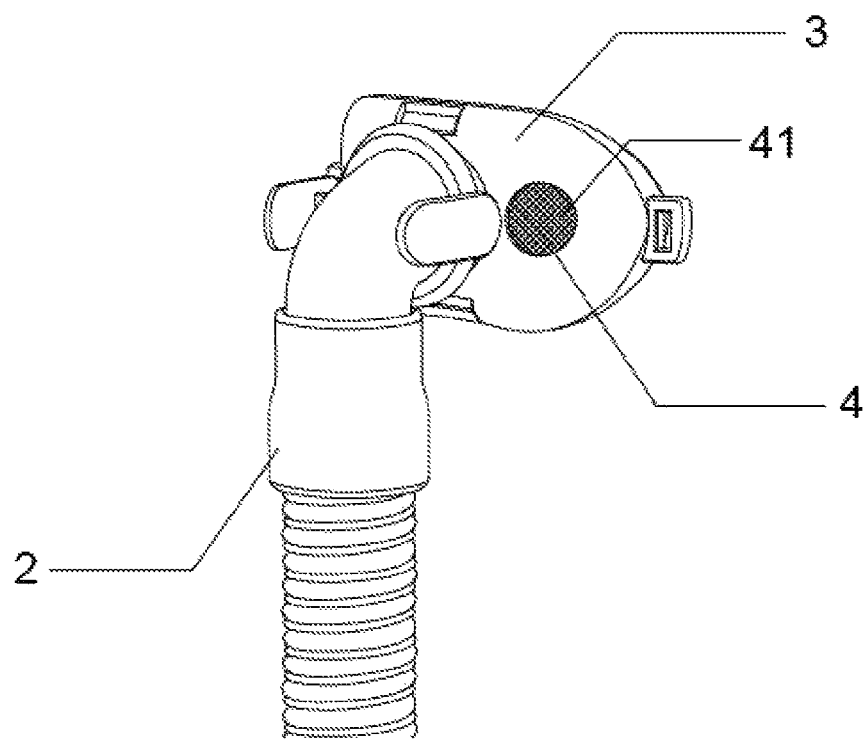
FIG. 3 is a three-dimensional combined schematic diagram of the device for delivering gas provided in Embodiment 1.

This embodiment provides a device 1 for delivering gas, as shown in FIGS. 1, 2, and 3. FIG. 1 is a front view of the device 1 for delivering gas provided in this embodiment. FIG. 2 is a three-dimensional exploded schematic diagram of the device 1 for delivering gas provided in this embodiment. FIG. 3 is a three-dimensional combined schematic diagram of the device 1 for delivering gas provided in this embodiment. As shown in FIGS. 1, 2, and 3, the device 1 includes a frame 3, a gas delivery hose 2, and a noise reduction component 4. The frame 3 has a first side connecting a nasal mask 6 and a second side opposite to the first side. The frame 3 and the nasal mask 6 form a cavity. The gas delivery hose 2 has an exhaust end connector 21 detachably connected to the second side of the frame 3 and an intake end connector 22 for connecting to the hose of a continuous positive airway pressure breathing machine. The two ends of the exhaust end connector 21 are respectively connected to the intake end connector 22 and the cavity. The noise reduction component 4 includes a ventilation port 42 and a muffler 41. The ventilation port 42 is provided in the frame 3 and communicates with the cavity. The muffler 41 is connected to the frame 3 and covers the ventilation port 42. The muffler 41 has a first surface 411 facing the external environment and a second surface 412 opposite to the first surface 411. The first surface 411 has a first breathable area exposed to the external environment, and the second surface 412 has a second breathable area exposed to the cavity. The muffler 41 also has multiple breathable channels communicating the first breathable area and the second breathable area to allow gas in the cavity to be discharged to the external environment through the muffler 41.

Figure 4:
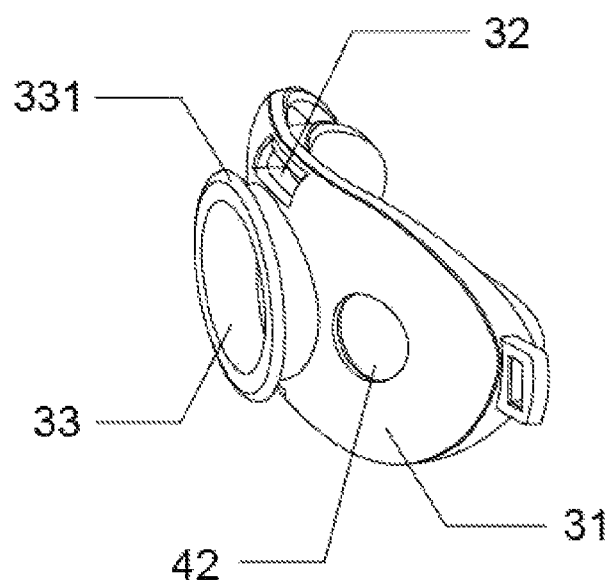
FIG. 4 is a three-dimensional structural schematic diagram of the frame provided in Embodiment 1.

As shown in FIG. 4, a three-dimensional structural schematic diagram of the frame provided in this embodiment, the frame 3 includes a frame body 31, a cylindrical protruding interface 33 provided in the frame body 31, and a buckle connector 32. The edge of the cylindrical protruding interface 33 is outwardly folded to form a circular convex buckle 331. The two ventilation ports 42 are respectively provided on the opposite sides of the cylindrical protruding interface 33. The buckle connector 32 is provided in the frame body 31. The frame 3 also has two connecting ears on the opposite sides of the frame body 31 for connecting a headband 5.

Figure 5:
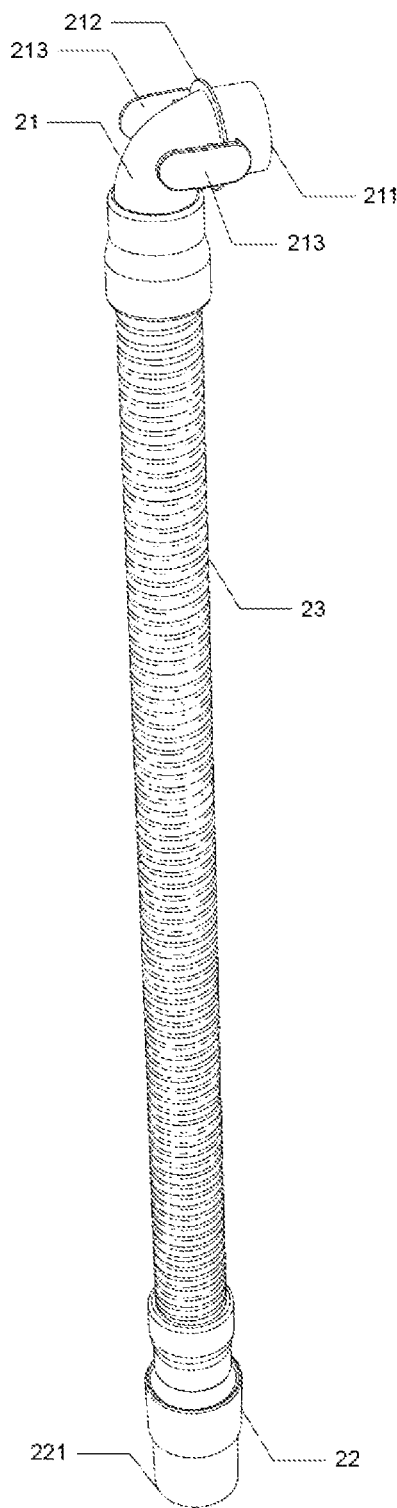
FIG. 5 is a three-dimensional structural schematic diagram of the gas delivery hose provided in Embodiment 1.

FIG. 5 shows a three-dimensional structural schematic diagram of the gas delivery hose 2 provided in this embodiment. The gas delivery hose 2 includes an intake end connector 22, a telescopic tube 23 connected to one end of the intake end connector 22, and an exhaust end connector 21 connected to the other end of the telescopic tube 23. The exhaust end connector 21 has a cylindrical first interface 211, a circular positioning barrier 212 formed around the outer side of the first interface 211, and a pair of symmetrically arranged hooking pieces 213.

Figure 6:
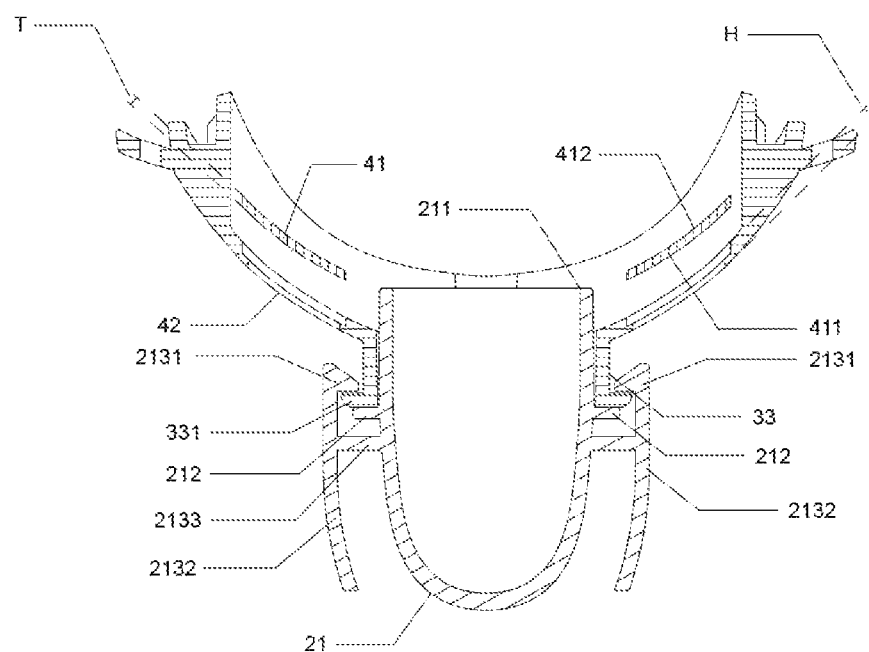
FIG. 6 is a sectional schematic diagram of A-A in FIG. 1.

FIG. 6 is a sectional schematic diagram at the A-A position in FIG. 1. In FIG. 6, the sectional structure of the exhaust end connector 21 combined with the frame 3 provided in this embodiment can be seen. It can be seen that the hooking piece 213 is provided with a hook portion 2131 at one end facing the first interface 211, and the surface facing the first interface 211 of the hook portion 2131 is inclined. The surface of the hook portion 2131 facing away from the first interface 211 is located on the side of the circular positioning barrier 212 facing towards the first interface 211. The gap width between the surface of the hook portion 2131 facing away from the first interface 211 and the circular positioning barrier 212 can accommodate the buckle 331. When the first interface 211 is inserted into the cylindrical protruding interface 33, the buckle 331 is exactly embedded between the hook portion 2131 and the circular positioning barrier 212. Because the opposite sides of the buckle 331 along the axial direction are respectively supported by the hook portion 2131 and the circular positioning barrier 212, the exhaust end connector 21 is not easy to loosen in the axial direction. Because the buckle 331 is circular and the central axis of the buckle 331 is collinear with the central axis of the cylindrical protruding interface 33, the exhaust end connector 21 is allowed to rotate at any angle relative to the cylindrical protruding interface 33. In addition, in FIG. 6, it can be seen that the hooking piece 213 has an extension at the end away from the first interface 211, forming a pressing portion 2132. The pressing portion 2132 is connected to a supporting piece 2133 between the hook portion 2131. The supporting piece 2133 is fixedly connected to the outer side wall of the first interface 211. It can be understood that when the pressing portion 2132 is pressed, the hook portion 2131 will turn outward until it separates from and does not contact the buckle 331, allowing the user to easily remove the exhaust end connector 21 from the cylindrical protrusion interface 33 of the frame 3. In this way, a detachable and rotatable connection between the exhaust end connector 21 and the frame 3 is achieved.

In summary, the device 1 for delivering gas adopts the above-mentioned technical solution to transport pressurized gas through the breathing machine hose to the gas delivery hose 2, and then transports the pressurized gas to the frame 3 and nasal mask 6 through the gas delivery hose 2, thereby delivering it to the patient's respiratory cavity to achieve the desired therapeutic effect. The advantage of this application is that the device 1 for delivering gas is equipped with at least one noise reduction component 4 to replace the existing form of directly opening holes on the frame 3. The key point is that the noise reduction component 4 includes a ventilation port 42 and a muffler 41. The ventilation port 42 penetrates the frame 3 to connect the cavity with the external environment. The muffler 41 is connected to the frame 3 and covers the ventilation port 42. It can be made of noise reduction materials. Specifically, the muffler 41 has a first surface 411 and a second surface 412. The first surface 411 faces the external environment, and the second surface 412 faces the cavity (also known as the pressure chamber) and the face. Moreover, the muffler 41 has multiple breathable channels that connect the first breathable area and the second breathable area. It can be understood that when the gas exhaled by the human body enters the cavity, it forms another exhaust flow path different from the pressurized airflow in the cavity. The exhaled gas is smoothly guided to the noise reduction component 4 and enters the external environment through the breathable channels of the muffler 41. That is to say, the muffler 41 allows the gas in the cavity to be continuously discharged to the external environment. Therefore, when wearing the device 1, the exhaled gas, such as carbon dioxide, can be continuously discharged from the inside of the cavity (referred to as a pressurized chamber in this field) to the external environment through the noise reduction component 4. Among them, the multiple breathable channels included in the muffler 41 can disperse the gas flow, making the concentrated gas flow into smaller and less turbulent streams, thereby significantly reducing the sound when the gas in the cavity is discharged to the external environment through the muffler 41, and the noise reduction effect is significant. In addition, because the exhaled gas from the human body can continuously flow from the inside of the cavity to the external environment, setting the noise reduction component 4 can reduce the probability of the exhaled carbon dioxide being inhaled again by the user, while maintaining the therapeutic pressure in the cavity during use.

It's also worth mentioning that there are other products on the market that use textiles on frame 3 to achieve exhaust function. However, in these products, the gas delivery hose 2 and the frame 3 are permanently connected and cannot be detached or rotated. In the proposed technical solution, the exhaust end connector 21 of the gas delivery hose 2 and the frame 3 can be separated, providing several advantages.

Firstly, it's more convenient for daily wearing and taking off. When leaving the bed briefly, users can detach the gas delivery hose 2 without removing the frame 3 that holds the nasal mask 6 in place, thus avoiding the cumbersome process of readjusting the nasal mask 6 and the frame 3.

Secondly, the integrated frame 3 and gas delivery hose 2 cannot be separated, which makes cleaning difficult and can leave dead corners or residuals from cleaning agents, leading to the easier growth of bacteria. The detachable design allows for the separation of the gas delivery hose 2 and the frame 3, making it easier to clean and dry.

Thirdly, the integrated frame 3 and gas delivery hose 2 are more easily damaged, and in terms of their service life, the gas delivery hose 2 is more susceptible to stretching and punctures due to its material, making it more prone to damage. If the gas delivery hose 2 is damaged, the frame 3 also needs to be replaced, which reduces the service life of the entire device 1. Adding a detachable design to the application modularizes the product, allowing for the search for replacement parts if one component is damaged, without the need to replace the entire device 1, thus improving the product's service life while also saving resources and reducing the user's cost of use.

Furthermore, the surface area of the first breathable area is 3% to 72% of the outer surface area of the frame 3, where the outer surface of the frame 3 is located on the surface of the second side. The contour of the ventilation port 42 can be circular, elliptical, rectangular, square, or triangular. In this way, the muffler 41 has sufficient area for the gas in the cavity to be discharged smoothly to the external environment without compromising the overall structural strength of the frame 3. The airflow direction of the gas discharged from the muffler 41 should be avoided from blowing towards the user's face or other parts that may affect the user's sleep, and also avoid blocking the noise reduction component 4 when sleeping on the side.

Moreover, referring back to FIG. 6, the frame 3 has a shielding wall with a thickness less than or equal to 7 mm, which is a rigid structure. The ventilation port 42 is provided on the shielding wall, so that the depth H of the ventilation port 42 is less than or equal to 7 mm. Continuing to refer to FIG. 6, the muffler 41 is thin and its thickness T is less than or equal to 10 mm. The surface area of the first breathable area or the second breathable area is at or between 1-21 cm$^2$. The weight of the muffler 41 is less than or equal to 7.5 g. The noise-reducing net of the muffler 41 is made of one of the materials such as polyvinyl chloride, polypropylene, polytetrafluoroethylene or nylon. It should be noted that the material, thickness, and density of the muffler 41 determine its noise reduction effect, but the specific materials used should be jointly determined based on processing, aesthetics, and actual effects. The material of the muffler 41 should not be too thick. One reason is that excessive thickness will reduce the gas permeability, thereby failing to achieve the effect of exhaust, and another reason is that excessive thickness will affect the overall appearance and weight of the mask. Therefore, the thickness T of the noise-reducing material (i.e. muffler 41) should be at most 10 mm, and the weight should be at most 7.5 g, and the surface area of the first breathable area or the second breathable area should be at or between 1-21 cm$^2$. The thickness of the noise-reducing material refers to the vertical distance from the first surface 411 to the second surface 412 of the noise-reducing material. With this design, when the exhaled gas is guided r, to the noise reduction component 4 and the exhaled gas passes through the noise reduction component 4 and enters the external environment, the noise generated does not exceed 30 dB.

Figure 7A:
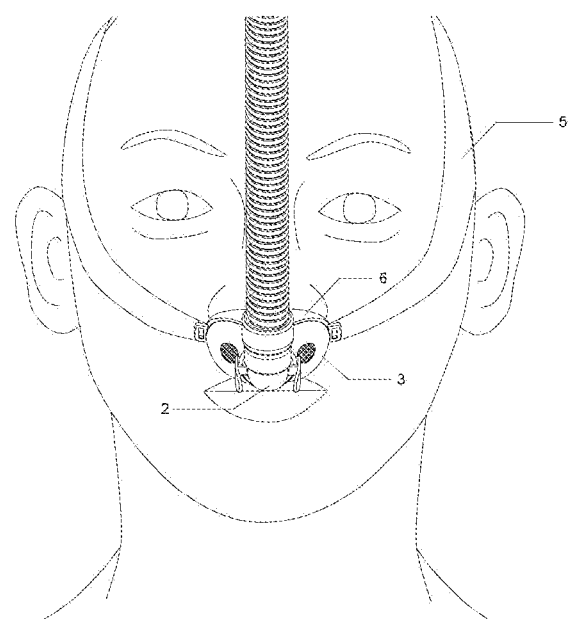
FIG. 7a is a reference diagram (1) of the use state of the device provided in Embodiment 1.
Figure 7B:
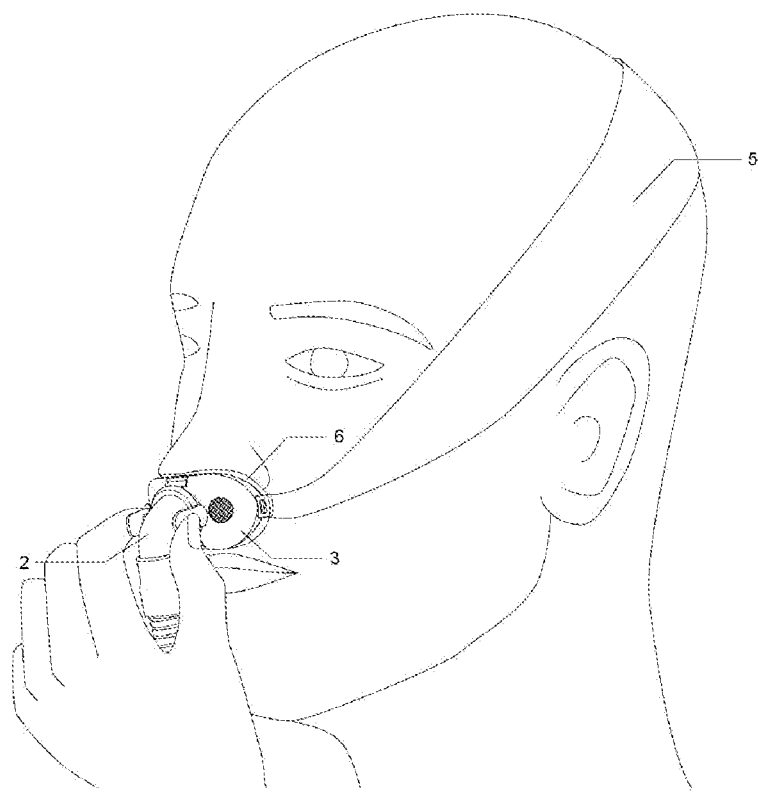
FIG. 7b is a reference diagram (2) of the use state of the device provided in Embodiment 1.

Further, the exhaust end connector 21 is connected to the second side of the frame 3 in a rotatable manner, while the intake end connector 22 is detachably and rotatably connected to the breathing machine. This allows for convenient multi-wearing methods. Moreover, the gas delivery hose 2 is also rotatably connected to the hose of a breathing machine through the intake end connector 22, and the two ends of the gas delivery hose 2 are designed to be rotatable, which facilitates the user to adjust the angle and position of the tube, avoiding entanglement of the gas delivery hose 2 and providing the user with various wearing options for a better user experience. Referring to FIG. 7a, which is a reference diagram (1) of the usage state of the device 1 provided in this embodiment, the gas delivery hose 2 can be rotated to an upward extension angle. Referring to FIG. 7b, which is a reference diagram (2) of the usage state of the device 1 provided in this embodiment, the delivery hose 2 can be rotated to a downward extension angle.

Additionally, the intake end connector 22 and the exhaust end connector 21 are connected by a telescopic tube 23, and the cross-sectional contour of the telescopic tube is circular. The outer diameter range of the telescopic tube 23 is at or between 10-40 mm, and the diameter range of the telescopic tube 23 is at or between 0.5-10 mm.

Moreover, the frame 3 is provided with a buckle connector 32, and the nasal mask 6 is detachably connected to the buckle connector 32. Here, the frame 3 is at least partially rigid, and the buckle connector 32 is provided on the rigid part of the frame 3, and the detachable connection between the frame 3 and the nasal mask 6 is achieved through the buckle connector 32.

Furthermore, the muffler 41 is fixedly connected to the frame 3. In this embodiment, the first surface 411 of the muffler 41 is fixedly connected to the inner surface of the frame 3, where the inner surface of the frame 3 is the surface located on the first side. In some other embodiments, the second surface 412 of the muffler 41 is fixedly connected to the outer surface of the frame 3, where the outer surface of the frame 3 is the surface located on the second side. Specifically, the connection between the muffler 41 and the frame 3 is achieved by adhesive, snap, knob, clip, ultrasonic bonding or heat pressing. As a result, the connection between the muffler 41 and the frame 3 is more stable and less prone to detachment.

Embodiment 2

Figure 8:
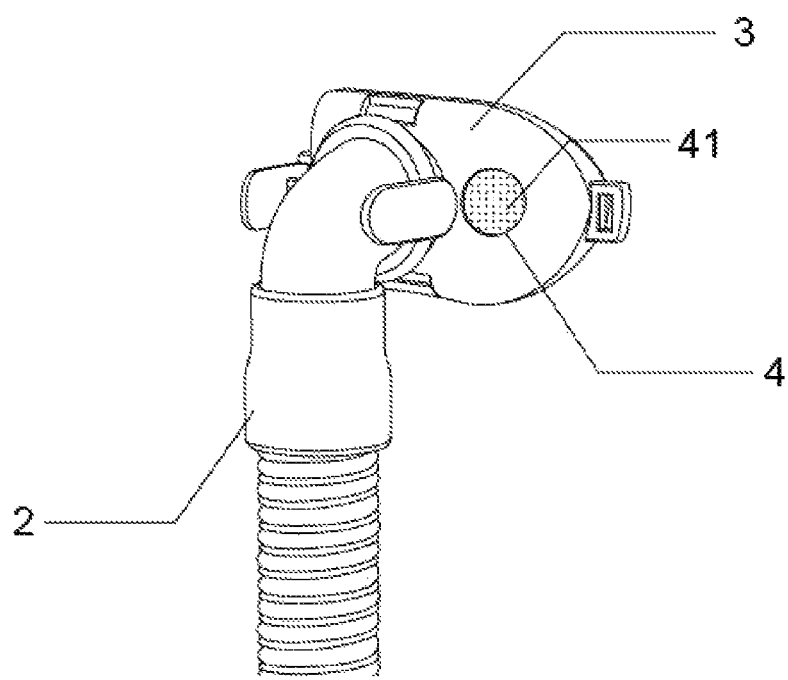
FIG. 8 is a three-dimensional combined schematic diagram of the device for delivering gas provided in Embodiment 2.

This embodiment provides a gas delivery device 1, which is different from Embodiment 1. Referring to FIG. 8, FIG. 8 is a three-dimensional combined schematic diagram of the device 1 for delivering gas provided in this embodiment. It can be seen in FIG. 8 that the muffler 41 is made of noise reducing cotton. Specifically, the noise reducing cotton is made of one of polyester, polypropylene, polyethylene, nylon, vinyl, and natural fabrics.

Embodiment 3

This example provides a gas delivery device 1, which is different from Embodiment 1. The noise reduction component 4 further includes a shell, and the muffler 41 is attached to one side surface of the shell facing the cavity. The outer shell is provided with multiple through exhaust ports, and the shell is detachably connected to the frame 3. Specifically, the shell and the frame 3 are connected by adhesive, snap, buckle, magic tape, knob, magnetic suction component or clip. Therefore, when it is found that the air permeability of the muffler 41 is reduced, it can be quickly replaced or cleaned without the need to process the entire frame 3.

Embodiment 4

Figure 9:
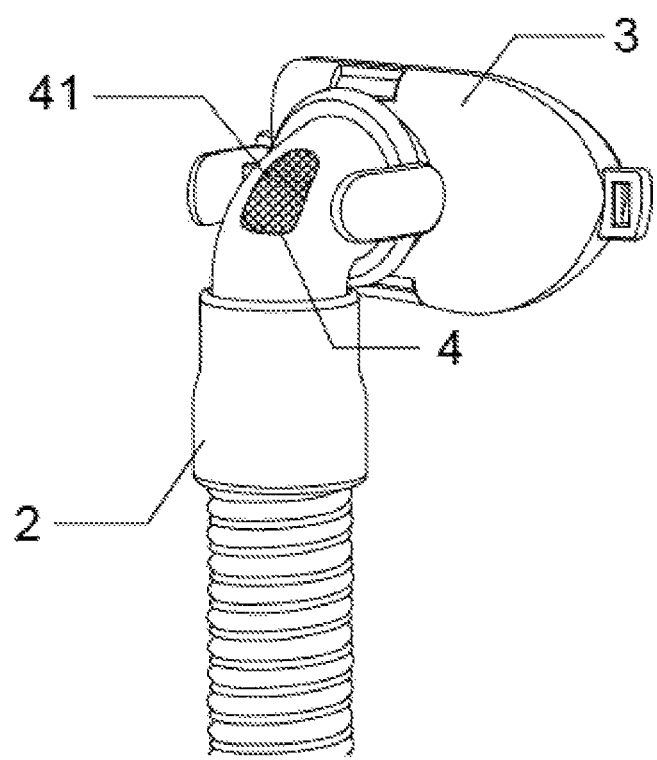
FIG. 9 is a three-dimensional combined schematic diagram of the device for delivering gas provided in Embodiment 4.

This embodiment provides a device 1 for delivering gas, which differs from Embodiment 1 in the design location of the noise reduction component 4. In this embodiment, the noise reduction component 4 is positioned on the exhaust end connector 21. FIG. 9 is a three-dimensional combined schematic diagram of the device 1 for delivering gas provided in this embodiment. Please also refer to FIGS. 1-3 for a comprehensive understanding. As shown in FIG. 9, the device 1 includes a frame 3, a gas delivery hose 2, and a noise reduction component 4.

The frame 3 has a first side connecting the nasal mask 6 and a second side opposite the first side, and the frame 3 and the nasal mask 6 form a cavity.

The gas delivery hose 2 has an exhaust end connector 21 detachably connectable to the second side of the frame 3 and an intake end connector 22 for connecting to the breathing machine hose. The two ends of the exhaust end connector 21 are respectively connected to the intake end connector 22 and the cavity.

The noise reduction component 4 includes a ventilation port 42 and a muffler 41. Crucially, the ventilation port 42 is opened on the exhaust end connector 21 and connected to the cavity. The muffler 41 is connected to the exhaust end connector 21 and covers the ventilation port 42. The muffler 41 has a first surface 411 facing the external environment and a second surface 412 opposite the first surface 411. The first surface 411 has a first breathable area exposed to the external environment, and the second surface 412 has a second breathable area exposed to the internal space of the exhaust end connector 21. The muffler 41 also has multiple breathable channels connecting the first breathable area and the second breathable area, allowing gas in the cavity to be discharged to the external environment through the muffler 41.

Clearly, when wearing the device 1, gas exhaled by the human body, such as carbon dioxide, can continuously be discharged from the internal space of the cavity (referred to as a pressurized chamber in the art) to the external environment through the noise reduction component 4. The multiple breathable channels contained in the muffler 41 can disperse the gas flow and make the flow into smaller and less turbulent streams, reducing the sound when the gas is discharged from the cavity to the external environment through the muffler 41, significantly reducing noise.

Embodiment 5

Figure 10:
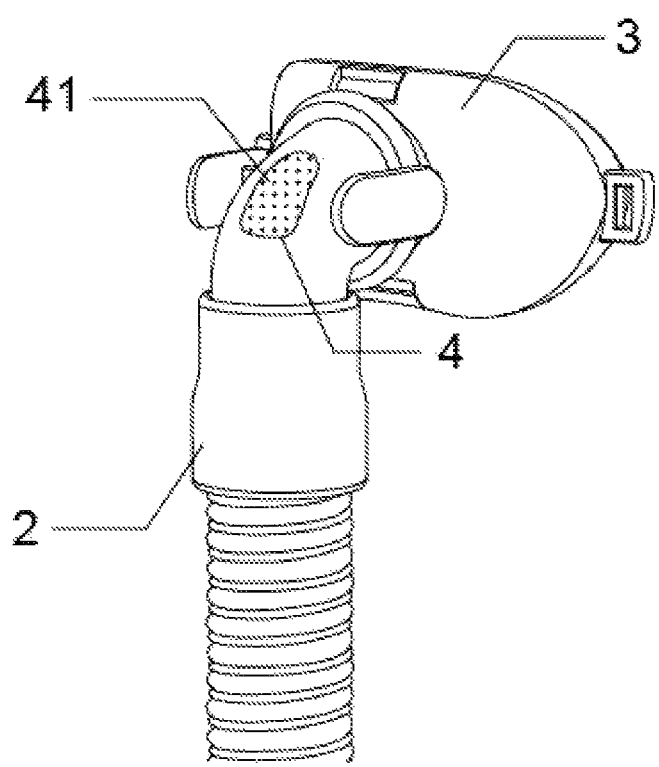
FIG. 10 is a three-dimensional combined schematic diagram of the device for delivering gas provided in Embodiment 5.

This embodiment provides a device 1 for delivering gas, which differs from Embodiment 4 in that, as shown in FIG. 10, the muffler 41 is made of noise-reducing cotton, which is made of one of polyester, polypropylene, polyethylene, nylon, vinyl, and natural fabric.

Aspects:

Any of Aspects 1-19 can be combined with any of Aspects 20-22, Aspect 20 can be combined with any of Aspects 1-19 and 21-22, Aspect 21 can be combined with any of Aspects 1-20 and 22, and Aspect 22 can be combined with any of Aspects 1-21.

Aspect 1: A device for delivering gas, comprising: a frame having a first side connecting a nasal mask and a second side opposite to said first side, wherein said frame and said nasal mask form a cavity; a gas delivery hose having an exhaust end connector detachably connectable to the second side of said frame and an intake end connector for connecting to a breathing machine hose, wherein both ends of said exhaust end connector are in communication with said intake end connector and said cavity, respectively; and a noise reduction component comprising a ventilation port and a muffler, wherein said ventilation port is provided on said frame and in communication with said cavity, and said muffler is connected to said frame and covers said ventilation port, said muffler having a first surface facing an external environment and a second surface opposite to said first surface, wherein said first surface has a first breathable area exposed to the external environment and said second surface has a second breathable area exposed to said cavity, and said muffler further having multiple breathable channels in communication with said first breathable area and said second breathable area, allowing gas within said cavity to be discharged from said muffler to the external environment.

Aspect 2. The device for delivering gas according to Aspect 1, wherein a surface area of said first breathable area is 3% to 72% of a surface area of an outer surface of said frame, wherein said outer surface is located on said second side.

Aspect 3. The device for delivering gas according to any of Aspects 1-2, wherein said frame has a shielding wall with a thickness of no more than 7 mm, and said ventilation port is provided on said shielding wall.

Aspect 4. The device for delivering gas according to any of Aspects 1-3, wherein said muffler is in a form of a thin sheet and has a thickness T of no more than 10 mm.

Aspect 5. The device for delivering gas according to any of Aspects 1-4, wherein an area of said first breathable area or said second breathable area is at or between 1 and 21 $cm^2$.

Aspect 6. The device for delivering gas according to any of Aspects 1-5 wherein a weight of said muffler is no more than 7.5 g.

Aspect 7. The device for delivering gas according to any of Aspects 1-6, wherein said exhaust end connector is rotatably connected to the second side of said frame.

Aspect 8. The device for delivering gas according to any of Aspects 1-7, wherein a contour of said ventilation port is circular, elliptical, rectangular, square, or triangular.

Aspect 9. The device for delivering gas according to any of Aspects 1-8, wherein the intake end connector and the exhaust end connector are connected by a telescopic tube, and a cross-sectional contour of the telescopic tube is circular.

Aspect 10. The device for delivering gas according to Aspect 9, wherein an outer diameter range of the telescopic tube is at or between 10-40 mm.

Aspect 11. The device for delivering gas according to any of Aspects 9-10, wherein a diameter range of the telescopic tube is at or between 0.5-10 mm.

Aspect 12. The device for delivering gas according to any of Aspects 1-11, wherein the frame is provided with a buckle connector, and the nasal mask is detachably connectable to the buckle connector.

Aspect 13. The device for delivering gas according to any of Aspects 1-12, wherein the intake end connector is detachably and rotatably connected to the breathing machine hose.

Aspect 14. The device for delivering gas according to any of Aspects 1-13, wherein the noise reduction component further comprises a shell, the muffler is attached to one side surface of the shell facing the cavity, the shell is provided with at least one through exhaust port, and the shell is detachably connectable to the frame.

Aspect 15. The device for delivering gas according to Aspect 14, wherein the shell is connected to the frame by adhesive, buckle, knob, clip, ultrasonic pressure bonding or compression, or heat or hot pressing.

Aspect 16. The device for delivering gas according to any of Aspects 1-15, wherein the muffler is fixedly connected to the frame.

Aspect 17. The device for delivering gas according to Aspect 16, wherein the muffler is connected to the frame by adhesive, buckle, knob, clip, ultrasonic pressure bonding or compression, or heat or hot pressing.

Aspect 18. The device for delivering gas according to any of Aspects 1-17, wherein the muffler is made of noise reducing cotton or noise reducing mesh.

Aspect 19. The device for delivering gas according to Aspect 18, wherein the noise reducing cotton is made of polyester, polypropylene, polyethylene, nylon, vinylon, or natural fabric; and the noise reducing mesh is made of polyvinyl chloride, polypropylene, polytetrafluoroethylene, or nylon.

Aspect 20. A device for delivering gas, comprising: a frame having a first side connecting a nasal mask and a second side opposite the first side, wherein the frame and the nasal mask form a cavity; a gas delivery hose having an exhaust end connector detachably connectable to the second side of said frame and an intake end connector for connection to a breathing machine hose, wherein two ends of the exhaust end connector are respectively connected to the intake end connector and the cavity; and a noise reduction component comprising a ventilation port and a muffler, wherein the ventilation port is opened in the exhaust end connector and connected to the cavity, and the muffler is connected to the exhaust end connector and covers the ventilation port, wherein the muffler has a first surface facing an external environment and a second surface opposite the first surface, the first surface having a first breathable area exposed to the external environment, and the second surface having a second breathable area exposed to an internal space of the exhaust end connector, and the muffler also having multiple breathable channels communicating with the first breathable area and the second breathable area configured to allow gas in the cavity to be discharged from the muffler to the external environment.

Aspect 21. A device for delivering gas, comprising: a frame having a first side connecting a nasal mask and a second side opposite the first side, wherein the frame and the nasal mask form a cavity; a gas delivery hose having an exhaust end connector detachably connectable to the second side of said frame and an intake end connector for connection to a breathing machine hose, wherein two ends of the exhaust end connector are respectively connected to the intake end connector and the cavity; and a noise reduction component comprising a ventilation port and a muffler, wherein the ventilation port is opened in the frame and connected to the cavity, and the muffler is connected to the frame and covers the ventilation port, wherein the muffler has a first surface facing an external environment and a second surface opposite the first surface, the first surface having a first breathable area exposed to the external environment, and the second surface having a second breathable area exposed to the cavity; the muffler also having multiple breathable channels communicating with the first breathable area and the second breathable area configured to allow gas in the cavity to be discharged from the muffler to the external environment; wherein a surface area of the first breathable area is 3% to 72% of a surface area of an outer surface of the frame, wherein the outer surface of the frame is surface located on the second side; and the frame has a shielding wall with a thickness of not more than 7 mm, and the ventilation port is opened in the shielding wall.

Aspect 22. A device for delivering gas, comprising: a frame having a first side connecting a nasal mask and a second side opposite the first side, wherein the frame and the nasal mask form a cavity; a gas delivery hose having an exhaust end connector detachably connectable to the second side of the frame and an intake end connector for connection with a breathing machine hose, wherein both ends of the exhaust end connector are in communication with the intake end connector and the cavity; and a noise reduction component comprising a ventilation port and a muffler, wherein the ventilation port is formed in the frame and communicates with the cavity, and the muffler is connected to the frame and covers the ventilation port, and the muffler has a first surface facing an external environment and a second surface opposite the first surface, wherein the first surface has a first breathable area exposed to the external environment, and the second surface has a second breathable area exposed to the cavity, and the muffler also has multiple breathable channels that connect the first breathable area and the second breathable area configured to allow gas inside the cavity to be discharged from the muffler to the external environment; wherein the muffler has a thickness T of less than or equal to 10 mm; an area of the first breathable area or the second breathable area is between 1-21 $cm^2$; and a weight of the muffler is less than or equal to 7.5 g.

Above, the embodiments of the disclosure have been described in conjunction with the accompanying drawings, but the disclosure is not limited to the specific embodiments described above, which are only illustrative rather than restrictive. Those skilled in the art, based on the inspiration of the disclosure, can make many variations within the scope of protection defined by the purpose of the disclosure and the claims, and all of these variations are within the protection of the disclosure.

The invention claimed is:

1. A device for delivering gas, comprising:
    a frame having a first side connecting a nasal mask and a second side opposite to said first side, said second side comprising a protruding interface, wherein said frame and said nasal mask form a cavity, and said frame comprising a ventilation port;
    a gas delivery hose having an exhaust end connector detachably connectable to the second side of said frame via an interface that is insertable into the protruding interface on the second side, and an intake end connector for connecting to a breathing machine hose, wherein the exhaust end connector is in communication with said intake end connector and said cavity; and
    a noise reduction component comprising a muffler, wherein said ventilation port provided on said frame and the muffler are in communication with said cavity, and said muffler is connectable to said frame to cover an inner side of said ventilation port, said muffler having a first surface facing an external environment and a second surface opposite to said first surface, wherein said first surface has a first breathable area exposed to the external environment and said second surface has a second breathable area exposed to said cavity, and said muffler further having multiple breathable channels in communication with said first breathable area and said second breathable area, allowing gas within said cavity to be discharged from said muffler to the external environment.

2. The device for delivering gas according to claim 1, wherein a surface area of said first breathable area is 3% to 72% of a surface area of an outer surface of said frame, wherein said outer surface is located on said second side.

3. The device for delivering gas according to claim 1, wherein said frame has a shielding wall with a thickness of no more than 7 mm, and said ventilation port is provided on said shielding wall.

4. The device for delivering gas according to claim 1, wherein said muffler is in a form of a thin sheet and has a thickness T of no more than 10 mm.

5. The device for delivering gas according to claim 1, wherein an area of said first breathable area or said second breathable area is at or between 1 and 21 $cm^2$.

6. The device for delivering gas according to claim 1, wherein a weight of said muffler is no more than 7.5 g.

7. The device for delivering gas according to claim 1, wherein said exhaust end connector is rotatably connected to the second side of said frame.

8. The device for delivering gas according to claim 1, wherein a contour of said ventilation port is circular, elliptical, rectangular, square, or triangular.

9. The device for delivering gas according to claim 1, wherein the intake end connector and the exhaust end connector are connected by a telescopic tube, and a cross-sectional contour of the telescopic tube is circular.

10. The device for delivering gas according to claim 9, wherein an outer diameter range of the telescopic tube is at or between 10-40 mm.

11. The device for delivering gas according to claim 9, wherein a diameter range of the telescopic tube is at or between 0.5-10 mm.

12. The device for delivering gas according to claim 1, wherein the frame is provided with a buckle connector, and the nasal mask is detachably connectable to the buckle connector.

13. The device for delivering gas according to claim 1, wherein the intake end connector is detachably and rotatably connected to the breathing machine hose.

14. The device for delivering gas according to claim 1, wherein the muffler is fixedly connected to the frame.

15. The device for delivering gas according to claim 14, wherein the muffler is connected to the frame by adhesive, buckle, knob, clip, ultrasonic pressure bonding or compression, or heat or hot pressing.

16. The device for delivering gas according to claim 1, wherein the muffler is made of cotton or mesh.

17. The device for delivering gas according to claim 16, wherein the cotton is made of polyester, polypropylene, polyethylene, nylon, vinylon, or natural fabric; and the mesh is made of polyvinyl chloride, polypropylene, polytetrafluoroethylene, or nylon.

18. A device for delivering gas, comprising:
a frame having a first side connecting a nasal mask and a second side opposite the first side, said second side comprising a protruding interface, wherein the frame and the nasal mask form a cavity;
a gas delivery hose having an exhaust end connector detachably connectable to the second side of said frame via an interface that is insertable into the protruding interface on the second side, and an intake end connector for connection to a breathing machine hose, wherein the exhaust end connector is connected to the intake end connector and the cavity; and
a noise reduction component comprising a muffler,
wherein the exhaust end connector includes a ventilation port that is connected to the cavity, and the muffler is connectable to the exhaust end connector and covers an inner side of the ventilation port, wherein the muffler has a first surface facing an external environment and a second surface opposite the first surface, the first surface having a first breathable area exposed to the external environment, and the second surface having a second breathable area exposed to an internal space of the exhaust end connector, and the muffler also having multiple breathable channels communicating with the first breathable area and the second breathable area configured to allow gas in the cavity to be discharged from the muffler to the external environment.

19. A device for delivering gas, comprising:
a frame having a first side connecting a nasal mask and a second side opposite the first side, said second side comprising a protruding interface, wherein the frame and the nasal mask form a cavity, and said frame comprising a ventilation port;
a gas delivery hose having an exhaust end connector detachably connectable to the second side of said frame via an interface that is insertable into the protruding interface on the second side, and an intake end connector for connection to a breathing machine hose, wherein the exhaust end connector is connected to the intake end connector and the cavity; and
a noise reduction component comprising a muffler,
wherein the ventilation port is connected to the cavity, and the muffler is connectable to the frame to cover an inner side of the ventilation port,
wherein the muffler has a first surface facing an external environment and a second surface opposite the first surface, the first surface having a first breathable area exposed to the external environment, and the second surface having a second breathable area exposed to the cavity; the muffler also having multiple breathable channels communicating with the first breathable area and the second breathable area configured to allow gas in the cavity to be discharged from the muffler to the external environment;
wherein a surface area of the first breathable area is 3% to 72% of a surface area of an outer surface of the frame, wherein the outer surface of the frame is surface located on the second side; and
the frame has a shielding wall with a thickness of not more than 7 mm, and the ventilation port is opened in the shielding wall.

20. A device for delivering gas, comprising:
a frame having a first side connecting a nasal mask and a second side opposite the first side, said second side comprising an interface, wherein the frame and the nasal mask form a cavity, and said frame comprising a ventilation port;
a gas delivery hose having an exhaust end connector detachably connectable to the second side of the frame via an interface that is insertable into the interface on the second side, and an intake end connector for connection with a breathing machine hose, wherein the exhaust end connector is in communication with the intake end connector and the cavity; and
a noise reduction component comprising a muffler,
wherein the ventilation port communicates with the cavity, and the muffler is connectable to the frame and covers an inner side of the ventilation port, and the muffler has a first surface facing an external environment and a second surface opposite the first surface, wherein the first surface has a first breathable area exposed to the external environment, and the second surface has a second breathable area exposed to the cavity, and the muffler also has multiple breathable channels that connect the first breathable area and the second breathable area configured to allow gas inside the cavity to be discharged from the muffler to the external environment;
wherein the muffler has a thickness T of less than or equal to 10 mm;
an area of the first breathable area or the second breathable area is between 1-21 cm$^2$; and
a weight of the muffler is less than or equal to 7.5 g.

* * * * *